(12) United States Patent
Cheng et al.

(10) Patent No.: US 10,702,636 B2
(45) Date of Patent: Jul. 7, 2020

(54) MEDICAL DEVICE

(71) Applicant: Gyrus ACMI, Inc., Southborough, MA (US)

(72) Inventors: Ming J. Cheng, West Warwick, RI (US); Phillip R. Scruggs, Collierville, TN (US)

(73) Assignee: Gyrus ACMI, Inc., Southborough, MA (US)

( * ) Notice: Subject to any disclaimer, the term of this patent is extended or adjusted under 35 U.S.C. 154(b) by 155 days.

(21) Appl. No.: 15/691,810

(22) Filed: Aug. 31, 2017

(65) Prior Publication Data
US 2019/0060535 A1   Feb. 28, 2019

(51) Int. Cl.
| | |
|---|---|
| *A61M 1/00* | (2006.01) |
| *A61B 17/32* | (2006.01) |
| *A61M 39/28* | (2006.01) |
| *A61B 90/70* | (2016.01) |
| *A61B 1/12* | (2006.01) |

(52) U.S. Cl.
CPC ........... *A61M 1/0064* (2013.01); *A61B 17/32* (2013.01); *A61B 17/32002* (2013.01); *A61M 1/0039* (2013.01); *A61M 1/0041* (2013.01); *A61M 1/0045* (2014.02); *A61M 1/0062* (2013.01); *A61M 1/0072* (2014.02); *A61M 39/287* (2013.01); *A61B 1/125* (2013.01); *A61B 90/70* (2016.02); *A61B 2017/320004* (2013.01); *A61B 2017/32008* (2013.01); *A61B 2217/005* (2013.01); *A61B 2217/007* (2013.01); *A61M 1/0078* (2013.01); *A61M 2205/3337* (2013.01)

(58) Field of Classification Search
CPC .............. A61M 1/0064; A61M 1/0072; A61M 1/0062; A61M 1/0058; A61M 1/0078; A61M 1/0043; A61M 1/0045; A61M 1/0066; A61M 1/0039; A61M 1/0023; A61M 39/22; A61M 39/28; A61M 39/281; A61M 39/287; A61M 39/286; A61B 90/70; A61B 2090/701; A61B 2018/00916
See application file for complete search history.

(56) References Cited

U.S. PATENT DOCUMENTS

| | | | |
|---|---|---|---|
| 5,439,022 A | 8/1995 | Summers et al. | |
| 5,830,214 A * | 11/1998 | Flom ................. | A61B 18/1482 606/41 |
| 7,270,647 B2 | 9/2007 | Karpowicz et al. | |

(Continued)

*Primary Examiner* — Kevin C Sirmons
*Assistant Examiner* — Alexandra Lalonde
(74) *Attorney, Agent, or Firm* — Harrington & Smith (57) ABSTRACT

Provided is a medical device for clearing an obstruction from a surgical instrument or surgical site, the device comprising: a first hollow member configured to allow air or inert gas passage; a second hollow member having a distal end and a proximal end, the proximal end configured to be connectable to a vacuum or suction source; a housing member configured to receive both the first hollow member and the second hollow member; and a push button operably connected to the housing member; and an inflation bulb configured to be attachable to the housing member, wherein the push button is configured to disengage the first hollow member and occlude the second hollow member when depressed by a force, and/or wherein the push button and the inflation bulb are configured to be operable by one hand of an operator.

20 Claims, 6 Drawing Sheets

(56) References Cited

U.S. PATENT DOCUMENTS

| | | | | |
|---|---|---|---|---|
| 2005/0197645 A1* | 9/2005 | Karpowicz | ......... | A61M 1/0062 |
| | | | | 604/514 |
| 2006/0264995 A1* | 11/2006 | Fanton | ............. | A61B 17/32002 |
| | | | | 606/180 |
| 2013/0138096 A1* | 5/2013 | Benn | .................. | A61B 18/1206 |
| | | | | 606/33 |
| 2013/0165849 A1* | 6/2013 | Monty | .................. | A61M 3/022 |
| | | | | 604/30 |
| 2013/0289595 A1 | 10/2013 | Edwards et al. | | |
| 2017/0100526 A1* | 4/2017 | Teng | .................. | A61M 1/0062 |

* cited by examiner

MEDICAL DEVICE

FIELD

The present disclosure relates generally to a medical device for clearing an obstruction from a surgical instrument or surgical site. More particularly, the disclosure relates to a medical device that utilizes a squeeze bulb and a suction line to clear an obstruction from a surgical instrument or from a surgical site during a surgical procedure.

BACKGROUND

Surgical instruments used to shave, cut, resect, abrade and/or remove tissue, bone and or other bodily materials are known. Once the tissue, bone and/or any other bodily materials are cut, it is necessary to remove them from the surgical site. This is typically accomplished through an inner lumen provided in the surgical instrument that is connected to a suction source. Existing surgical instrument may utilize a one-way suction line to aspirate tissue from the surgical site. It is often the case that the tissue forms a clog in the aspiration pathway (most often in the distal end of the surgical instrument). One way to remove the clog is for the person using the surgical instrument to remove the instrument from the surgical site and insert a stylet into the cutting window to force the clog through the cutting portion and into the inner lumen to be aspirated. However, this is often a time-consuming and tedious process, particularly over the course of a surgical procedure in which the surgeon may have to remove multiple clogs. Furthermore, removing and reinserting the surgical instrument is traumatic to the surgical site.

Cleaning functions such as irrigation, suction, or both may also be provided to or incorporated with a surgical instrument during a procedure in order to maintain the surgical instrument clean, which typically requires connecting various individual cables, tubes, lines, ports, etc. to the instrument. The various individual cables, tubes, lines, ports, etc. connected to the surgical instrument may however interfere with a doctor or surgeon performing the medical procedure, which may undesirably add additional time and/or complications to the procedure. Also, by connecting various individual cables, tubes, lines, ports, etc. to the surgical instrument, selective application of irrigation fluid, suction, or both may be difficult to control.

Therefore, in view of the above-mentioned problems associated with clearing clogs from a surgical instrument, it is desirable to develop ways of clearing clogs quickly and efficiently during a surgical procedure.

SUMMARY

In one embodiment, the disclosure provides a medical device comprising: a first hollow member configured to allow air or inert gas passage; a second hollow member having a distal end and a proximal end, the proximal end configured to be connectable to a vacuum or suction source; a housing member configured to receive both the first hollow member and the second hollow member; and a push button operably connected to the housing member, wherein the push button is configured to occlude the first hollow member and disengage the second hollow member when the push button is in its resting position.

In one embodiment, the disclosure provides a medical device comprising: a first hollow member configured to allow air or inert gas passage; a second hollow member having a distal end and a proximal end, the proximal end configured to be connectable to a vacuum or suction source; a housing member configured to receive both the first hollow member and the second hollow member; and a push button operably connected to the housing member, wherein the push button is configured to disengage the first hollow member and occlude the second hollow member when the push button is depressed by a force.

In one embodiment, the disclosure provides a medical device comprising: a first hollow member configured to allow air or inert gas passage; a second hollow member having a distal end and a proximal end, the proximal end configured to be connectable to a vacuum or suction source; a housing member configured to receive both the first hollow member and the second hollow member; and a push button operably connected to the housing member, wherein the push button is configured to disengage the first hollow member and occlude the second hollow member when depressed by a force and occlude the first hollow member and disengage the second hollow member when the depressing force is removed or absent.

In one embodiment, the disclosure provides a medical device comprising: a first hollow member configured to allow air or inert gas passage; a second hollow member having a distal end and a proximal end, the proximal end configured to be connectable to a vacuum or suction source; a housing member configured to receive both the first hollow member and the second hollow member; and a push button operably connected to the housing member; and an inflation bulb configured to be attachable to the housing member, wherein the inflation bulb and the push button are configured to be operable by one hand of an operator.

In one embodiment, the disclosure provides a medical device comprising: a first hollow member configured to allow air or inert gas passage; a second hollow member having a distal end and a proximal end, the proximal end configured to be connectable to a vacuum or suction source; a housing member configured to receive both the first hollow member and the second hollow member; and a push button operably connected to the housing member; and an inflation bulb configured to be attachable to the housing member, wherein the push button is configured to disengage the first hollow member and occlude the second hollow member when depressed by a force and occlude the first hollow member and disengage the second hollow member when the depressing force is removed or absent, and wherein the inflation bulb and the push button are configured to be operable by one hand of an operator.

In one embodiment, the disclosure also provides a medical or surgical system, the system comprising a medical device as described herein, a surgical or medical instrument, a vacuum or suction source, and an irrigation source.

In one embodiment, the disclosure further provides a method for clearing an obstruction from a surgical instrument or surgical site, the method including providing a medical device comprising a first hollow member configured to allow air or inert gas passage; a second hollow member configured to be connectable to a vacuum or suction source; a housing member configured to receive both the first hollow member and the second hollow member; a push button operably connected to the housing member; and an inflation bulb configured to be attachable to the housing member. The method also includes providing a surgical instrument for cutting, resecting, shaving, and/or removing tissue. The method also includes providing a vacuum or suction source. The method also includes providing an irrigation source. The method also includes providing proper connections between the medical device as described herein, the surgical instrument, the vacuum or suction source, and the irrigation source. The method ultimately includes removing an obstruction from the surgical instrument or from a surgical site by turning on the surgical instrument to perform cutting, resecting, shaving, and/or removing tissue as needed, turning on the irrigation source and the vacuum source as needed, and depressing the push button and squeezing the inflation bulb at a proper frequency to clear an obstruction from the surgical instrument or the surgical site.

DETAILED DESCRIPTION

The explanations and illustrations presented herein are intended to acquaint others skilled in the art with the disclosure, its principles, and its practical applications. Those skilled in the art may adapt and apply the disclosure in numerous forms, as may be best suited to the requirements of a particular use. The specific embodiments of the present disclosure as set forth are not intended to be exhaustive or limiting of the invention. The scope of the invention should be determined not with reference to the above description, but should be determined with reference to the appended claims, along with the full scope of equivalents to which such claims are entitled.

The terms "one embodiment", "an embodiment", "another embodiment", "some embodiments", "other embodiments", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or", unless context clearly indicates otherwise.

The term "such as" is used herein to mean, and is used interchangeably, with the phrase "such as but not limited to". Unless specifically stated or obvious from context, as used herein, the term "about" is understood as within a range of normal acceptance in the art, for example within standard deviations of the mean.

The term "proximal" is herein used to mean a position or direction closest to a user of the device and is in a position or direction opposite to the term "distal".

The term "distal" is herein used to mean a position or direction furthest away from a user of the device and is a position or direction opposite to the term "proximal".

All numeric values are herein assumed to be modified by the term "about" whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. Even more specifically, "about" can be understood as within 10%, 9%, 8%, 7%, 6%, 5%, 4%, 3%, 2%, 1%, 0.5%, 0.1%, 0.05%, or 0.01% of the stated value. Unless otherwise stated, all ranges include both endpoints and all numbers between the endpoints. The use of "about" or "approximately" in connection with a range applies to both ends of the range. Thus, "about 10 to 30" is intended to cover "about 10 to about 30", inclusive of at least the specified endpoints.

In one embodiment, the disclosure provides a medical device comprising: a first hollow member configured to allow air or inert gas passage; a second hollow member having a distal end and a proximal end, the proximal end configured to be connectable to a vacuum or suction source; a housing member configured to receive both the first hollow member and the second hollow member; and a push button operably connected to the housing member, wherein the push button is configured to occlude the first hollow member and disengage the second hollow member when the push button is in its resting position. In an embodiment, the housing member is configured to have a first section and a second section. In an embodiment, the push button is configured to be disposed in the first section of the housing member. In an embodiment, the distal end of the second hollow member is configured to be connectable to a surgical instrument. In an embodiment, the surgical instrument comprises an irrigation line.

In one embodiment, the disclosure provides a medical device comprising: a first hollow member configured to allow air or inert gas passage; a second hollow member having a distal end and a proximal end, the proximal end configured to be connectable to a vacuum or suction source; a housing member configured to receive both the first hollow member and the second hollow member; and a push button operably connected to the housing member, wherein the push button is configured to disengage the first hollow member and occlude the second hollow member when the push button is depressed by a force. In an embodiment, the housing member is configured to have a first section and a second section. In an embodiment, the push button is configured to be disposed in the first section of the housing member. In an embodiment, the distal end of the second hollow member is configured to be connectable to a surgical instrument. In an embodiment, the surgical instrument comprises an irrigation line.

In one embodiment, the disclosure provides a medical device comprising: a first hollow member configured to allow air or inert gas passage; a second hollow member having a distal end and a proximal end, the proximal end configured to be connectable to a vacuum or suction source; a housing member configured to receive both the first hollow member and the second hollow member; and a push button operably connected to the housing member, wherein the push button is configured to disengage the first hollow member and occlude the second hollow member when depressed by a force and occlude the first hollow member and disengage the second hollow member when the depressing force is removed or absent. In an embodiment, the housing member is configured to have a first section and a second section. In an embodiment, the push button is configured to be disposed in the first section of the housing member. In an embodiment, the distal end of the second hollow member is configured to be connectable to a surgical instrument. In an embodiment, the surgical instrument comprises an irrigation line.

In one embodiment, the disclosure provides a medical device comprising: a first hollow member configured to allow air or inert gas passage; a second hollow member having a distal end and a proximal end, the proximal end configured to be connectable to a vacuum or suction source; a housing member configured to receive both the first hollow member and the second hollow member; and a push button operably connected to the housing member; and an inflation bulb configured to be attachable to the housing member, wherein the inflation bulb and the push button are configured to be operable by one hand of an operator. In an embodiment, the inflation bulb is configured to have two openings: one of the two openings configured to be attached to the housing member. In an embodiment, one of the two openings of the inflation bulb is configured to have a one way check valve. In an embodiment, one of the two openings of the inflation bulb is configured to have an additional one way gas inlet. In an embodiment, the housing member is configured to have a first section and a second section. In an embodiment, the push button is configured to be disposed in the first section of the housing member. In an embodiment, the distal end of the second hollow member is configured to be connectable to a surgical instrument. In an embodiment, the surgical instrument comprises an irrigation line.

In one embodiment, the disclosure provides a medical device comprising: a first hollow member configured to allow air or inert gas passage; a second hollow member having a distal end and a proximal end, the proximal end configured to be connectable to a vacuum or suction source; a housing member configured to receive both the first hollow member and the second hollow member; and a push button operably connected to the housing member; and an inflation bulb configured to be attachable to the housing member, wherein the push button is configured to disengage the first hollow member and occlude the second hollow member when depressed by a force and occlude the first hollow member and disengage the second hollow member when the depressing force is removed or absent, and wherein the inflation bulb and the push button are configured to be operable by one hand of an operator. In an embodiment, the inflation bulb is configured to have two openings: one of the two openings configured to be attached to the housing member. In an embodiment, one of the two openings of the inflation bulb is configured to have a one way check valve. In an embodiment, one of the two openings of the inflation bulb is configured to have an additional one way gas inlet. In an embodiment, the housing member is configured to have a first section and a second section. In an embodiment, the push button is configured to be disposed in the first section of the housing member. In an embodiment, the distal end of the second hollow member is configured to be connectable to a surgical instrument. In an embodiment, the surgical instrument comprises an irrigation line.

In one embodiment, the disclosure provides a medical device comprising: a first hollow member configured to allow air or inert gas passage; a second hollow member having a distal end and a proximal end, the proximal end configured to be connectable to a vacuum or suction source; a housing member having a first section and a second section, the housing member configured to receive both the first hollow member and the second hollow member; a push button disposed at the first section of the housing member; and an inflation bulb having two openings, one of the two openings configured to be attached to the second section of the housing member, wherein the push button is configured to disengage the first hollow member and occlude the second hollow member when depressed by a force and occlude the first hollow member and disengage the second hollow member when the depressing force is removed or absent. In an embodiment, the other opening of the inflation bulb is configured to have a one way check valve. In an embodiment, the other opening of the inflation bulb is configured to have an additional one way gas inlet. In an embodiment, the distal end of the second hollow member is configured to be connectable to a surgical instrument. In an embodiment, the surgical instrument comprises an irrigation line.

In one embodiment, the disclosure provides a medical device comprising: a first hollow member configured to allow air or inert gas passage; a second hollow member having a distal end and a proximal end, the proximal end configured to be connectable to a vacuum or suction source; a housing member having a first section and a second section, the housing member configured to receive both the first hollow member and the second hollow member; a push button disposed at the first section of the housing member; and an inflation bulb having two openings, one of the two openings configured to be attached to the second section of the housing member, wherein the inflation bulb and the push button are configured to be operable by one hand of an operator. In an embodiment, the other opening of the inflation bulb is configured to have a one way check valve. In an embodiment, the other opening of the inflation bulb is configured to have an additional one way gas inlet. In an embodiment, the distal end of the second hollow member is configured to be connectable to a surgical instrument. In an embodiment, the surgical instrument comprises an irrigation line.

In one embodiment, the disclosure provides a medical device comprising: a first hollow member configured to allow air or inert gas passage; a second hollow member having a distal end and a proximal end, the proximal end configured to be connectable to a vacuum or suction source; a housing member having a first section and a second section, the housing member configured to receive both the first hollow member and the second hollow member; a push button disposed at the first section of the housing member; and an inflation bulb having two openings, one of the two openings configured to be attached to the second section of the housing member, wherein the push button is configured to disengage the first hollow member and occlude the second hollow member when depressed by a force and occlude the first hollow member and disengage the second hollow member when the depressing force is removed or absent, and wherein the inflation bulb and the push button are configured to be operable by one hand of an operator. In an embodiment, the other opening of the inflation bulb is configured to have a one way check valve. In an embodiment, the other opening of the inflation bulb is configured to have an additional one way gas inlet. In an embodiment, the distal end of the second hollow member is configured to be connectable to a surgical instrument. In an embodiment, the surgical instrument comprises an irrigation line.

In the above embodiments, the first hollow member is configured to have two open ends: one configured to be in fluid communication with the inflation bulb, the other configured to be connectable to a surgical instrument. In the above embodiments, the first hollow member is configured to be completely sealed, clamped, or occluded by the push button when the push button is in its resting position. As a result, when the push button is in its resting position, the first hollow member is blocked from fluid communication with the inflation bulb, and therefore will not interfere with the suction function of the medical device. In order to be completely or functionally sealed or clamped, the first hollow member may be disposed in a groove inside the housing member. This way, the first hollow member is vertically constrained or restricted, and yet movable along the longitudinal direction of the housing member when it is released into an open position from the push button. Other constraining mechanisms known in the art may also be employed. The first hollow member may be made of any suitable polymeric materials such as polyvinyl chloride (PVC), polyolefins, polyurethane, polyethylene terephthalate (PET), crosslinked polyethylene, nylon polymer, or their mixtures. The durometer of the first hollow member may be about 60 A to about 80 A, preferably about 65 A to about 70 A, or even more preferably 68 A. The outer diameter of the first hollow member may be about 3.0 to about 5.0 mm, preferably about 4.0 mm. The inner diameter of the first hollow member may be about 1.5 mm to about 3.0 mm, preferably about 2.4 mm. In all the above embodiments, the first hollow member may be made into any suitable shape, length, geometry, or size. Preferably, it is configured to be tubular.

In the above embodiments, the second hollow member is configured to be such that it is completely open or fully functional when the push button is in its resting position, and it is completely sealed or clamped when the push button is depressed to its full capacity. Consequently, when the first hollow member is in fluid communication with the inflation bulb, the suction function of the second hollow member will not interfere with the first hollow member when the push button is fully depressed. In order to be completely or functionally sealed or clamped, the second hollow member may be disposed in a groove inside the housing member. This way, the second hollow member is vertically constrained or restricted, and yet movable along the longitudinal direction of the housing member when needed or pulled. Other constraining mechanisms known in the art may also be employed. The second hollow tubular member may be made of any suitable elastic or polymeric materials such as polyvinyl chloride (PVC), polyolefins, polyurethane, polyethylene terephthalate (PET), crosslinked polyethylene, nylon polymer, silicone or their mixtures. The durometer of the second hollow member may be about 50 A to about 70 A, preferably about 60 A. The outer diameter of the second hollow member may be about 7.0 mm to about 9.0 mm, preferably about 8.0 mm. The inner diameter of the second hollow member may be from about 3.8 mm to about 5.8 mm, preferably about 4.8 mm. In all the above embodiments, the second hollow member may be made into any suitable shape, length, geometry, or size. Preferably, it is configured to be tubular.

In the above embodiments, the second hollow member may be alternatively called a suction line having a proximal end and a distal end. In the above embodiments, the proximal end of the second hollow member is configured to be connectable to a vacuum or suction source. In the above embodiments, the proximal end of the second hollow member may be configured to be connectable to a vacuum or suction source through the interior of the inflation bulb. In the above embodiments, the proximal end of the second hollow member may be configured to be connectable to a vacuum or suction source without going through the interior of the inflation bulb. In the above embodiments, the distal end of the second hollow member may be configured to be connectable to a surgical instrument. In the above embodiments, the distal end of the second hollow member may be configured to be connectable to a surgical instrument through a connecting member. The connecting member may be a Y connector. The connecting member may be other types known in the art.

In the above embodiments, the housing member may be made in any suitable size, dimension, shape or geometry. Preferably, it is made of a size or dimension such that an operator of the medical device as described herein can hold the housing member and the inflation bulb with just one hand. In the above embodiments, the housing member may be made from any suitable materials known in the art such as polymeric materials, metallic materials, and their combinations. The housing member may be made disposable, or reusable, and preferably made disposable.

In the above embodiments, the push button comprises a head and a stem. The stem of the push button may be configured to have two slots: one narrow, and the other wider. The narrow slot is configured to completely or functionally seal, block, or occlude the first hollow member when the push button is in its resting position or when the second hollow member is in use or operation. The wider slot is configured to be at least wider than the outer diameter of the first hollow member so that the first hollow member is in its full open configuration to allow air or an inert gas to flow through when the push button is fully pushed down. The head of the push button may be made of any suitable size, dimension, shape or geometry. The stem of the push button may be made of any suitable size, dimension, shape or geometry so long as it has the necessary two slots as described above.

The push button is configured to be restored by a biasing mechanism to its resting position after the pushing force is removed. The biasing member may be a spring, a resilient or biasing material, an elastic member, or a combination thereof. The biasing member may be a spring. The spring may be a helical coil spring. The spring may be configured to locate under the head of the push button. It may be configured to embrace the stem of the push button or outside of the stem. The push button may be configured to be in a lockable position by a locking mechanism after it is fully depressed in order for an operator to manipulate the inflation bulb for an extended period of time at a desired frequency. The locking mechanism may be a manual 2-position valve or any other mechanisms known in the art. The push button and the biasing spring may be operably secured to the housing member through the conventional means well known in the art.

In the above embodiments, the inflation bulb may be called an inflation balloon, an inflation device, an inflation ball, a squeeze ball, a squeeze bulb, and so on. In the above embodiments, the inflation bulb may be made of any suitable elastic or polymeric materials such as polyvinyl chloride (PVC), polyolefins, polyurethane, polyethylene terephthalate (PET), crosslinked polyethylene, nylon polymer, silicone or their mixtures. The inflation bulb may be configured at any suitable size, dimension, shape or geometry. Preferably, it may be made of a size of about 30 cc to about 80 cc, more preferably about 35-45 cc. Also preferably, the inflation bulb may be configured to accommodate one hand use by an operator with convenience. The inflation bulb may be configured to have two openings. One of the two openings is configured to possess a one way check valve and an additional one way gas inlet. The one way check valve is installed to assure smooth air flow from the outside or from a gas source into the inflation bulb when/if the one way gas inlet is clogged or blocked. The one way gas inlet only allows the air or inert gas to flow into the inflation bulb, but not the other way around. Accordingly, after air or inert gas is squeezed out of the inflation bulb, the outside air will automatically flow in due to the pressure difference. The one way gas inlet may be configured to be connectable to an inert gas when needed. The one way check valve may also be configured to be connectable to an inert gas source when/if needed. The openings of the inflation bulb are configured to be connectable and properly sealable to the housing member or the hollow members. The connection may be through adhesives, welding or snap fit or any other means known in the art.

In some embodiments, the first hollow member, the second hollow member, the push button, the housing member, and the inflation bulb may all be made of the same polymeric materials. In some embodiments, all of the above components may be made disposable or reusable, and preferably made disposable.

In one embodiment, the disclosure also provides a medical or surgical system, the system comprising a medical device as described herein, a surgical or medical instrument, a vacuum or suction source, and an irrigation source. In an embodiment, the surgical or medical instrument comprises an irrigation line configured to be connectable to the irrigation source supplying an irrigation fluid. In the above embodiments, the surgical or medical instrument may be shaver, a microdebrider, a surgical burr, a drill, an endoscope, an endoscope sheath, or a combination thereof. In the above embodiments, the medical or surgical system further comprises a pressure sensor for detecting a clog or obstruction during a surgical procedure. In the above embodiments, the medical device described herein may function to clean and protect a distal end of the surgical or medical instrument. In the above embodiments, the medical device described herein may function to clean an image sensor, a lens, or a device located at a distal viewing end of the surgical or medical instrument.

In the above embodiments, the irrigation source supplies, moves, communicates or transfers a fluid to the surgical or medical instrument. The irrigation fluid may function to move or flush particles, opaque fluids, contaminants, cut biological tissue, blood, obstructions, etc. or a combination thereof from a shaver, a microdebrider, a surgical burr, a drill, an endoscope, an endoscope sheath, an image sensor, a lens or device of an endoscope, a surgical site or a combination thereof. During an operation cycle, the fluid may be supplied, applied, circulated, transferred, communicated, and/or moved to the surgical or medical instrument continuously, selectively, intermittingly, or on-demand.

In the above embodiments, the vacuum or suction source of the surgical or medical system pulls, draws, communicates, or moves a fluid from or through the surgical or medical instrument. The vacuum or suction source may function to move, remove, or flush particles, opaque fluids, contaminants, cut biological tissue, blood, obstructions, irrigation fluid, or a combination thereof from a surgical or medical instrument, a point of interest, a surgical site, or from a combination thereof. The vacuum or suction source may function to perform a drying function, remove fluid spots, remove contaminants, or a combination thereof. The vacuum or suction source may be a vacuum pump, reversal of a motor, a common suction source, a hospital suction source or a combination thereof. The vacuum or suction source may be configured to pull, move, communicate and/or draw a sufficient amount of a fluid such as vacuum or suction through one or more suction lines, irrigation lines, or both to remove a predetermined amount of fluid in a predetermined amount of time. The suction source may pull, move, communicate and/or draw a vacuum or suction that is continuous, selective, on-demand, or a combination thereof through one or more suction lines.

In the above embodiment, the irrigation source, the vacuum or suction source, or both may be in constant communication, selective communication, or both with a medical or surgical instrument. In the above embodiments, the irrigation line and the vacuum or suction line (mainly the second hollow member of the medical device described herein) may be the same line or may be different lines. The medical or surgical system may include one or more control modules.

In one embodiment, the disclosure also provides a method for clearing an obstruction from a surgical or medical instrument, or surgical site, the method including providing a medical device comprising a first hollow member configured to allow air or inert gas passage; a second hollow member configured to be connectable to a vacuum or suction source; a housing member configured to receive both the first hollow member and the second hollow member; and a push button operably connected to the housing member. The method also provides a squeeze bulb configured to be connectable to the housing member. The method further includes providing a surgical instrument for cutting, resecting, shaving, and/or removing tissue. The method also includes providing a vacuum or suction source. The method also includes providing an irrigation line or source. The method further includes providing proper connections between the medical device, the medical or surgical instrument, the vacuum or suction source, and the irrigation line or source. The method ultimately includes removing an obstruction from the surgical or medical instrument by turning on the surgical or medical instrument to perform cutting, resecting, shaving, and/or removing tissue as needed; turning on the suction source and the irrigation source; and depressing the push button and squeezing the inflation bulb at a proper frequency to clear any obstruction from the surgical or medical instrument or the surgical site.

In one embodiment, the disclosure also provides a method for clearing an obstruction from a surgical instrument or surgical site, the method including providing a surgical device comprising a first hollow member configured to allow air or inert gas passage; a second hollow member configured to be connectable to a vacuum or suction source;

a housing member configured to receive both the first hollow member and the second hollow member; a push button operably connected to the housing member; and an inflation bulb configured to be attachable to the housing member. The method also includes providing a surgical instrument for cutting, resecting, shaving, and/or removing tissue. The method also includes providing a vacuum or suction source. The method also includes providing an irrigation line or source. The method also includes providing proper connections between the medical device, the surgical or medical instrument, the vacuum or suction source, and the irrigation source or line. The method ultimately includes removing an obstruction from the surgical or medical instrument by turning on the surgical or medical instrument to perform cutting, resecting, shaving, and/or removing tissue as needed, and depressing the push button and squeezing the inflation bulb at a proper frequency to clear any obstruction from the surgical or medical instrument or the surgical site.

In one embodiment, the disclosure also provides a method for clearing an obstruction from a surgical or medical instrument, or surgical site, the method including providing a surgical or medical system comprising a medical device as described herein, a surgical or medical instrument, a vacuum or suction source, and an irrigation source. The method also includes providing proper connections between the medical device, the medical or surgical instrument, the vacuum or suction source, and the irrigation source. The method finally turning on the surgical or medical system to perform cutting, resecting, shaving, and/or removing tissue as needed, and depressing the push button and squeezing the inflation bulb at a proper frequency to clear any obstruction from the surgical or medical instrument or the surgical site.

In the above embodiments, the medical device described herein uses air and suction in a coordinated fashion to remove any clog/obstruction from a surgical or medical instrument efficiently and conveniently. Squeezing/releasing the inflation bulb utilizes air or inert gas to blow out the debris and clear a pathway in the surgical or medical instrument. Pushing/releasing the push button should be maneuvered in coordination with squeezing/releasing the inflation bulb to ensure efficiency. The removal of clogs may be achieved by simple acts of an operator through a relatively simple structure as described herein.

In the above embodiments, the inflation bulb and the push button may be operated sequentially, or simultaneously, or concurrently, or separately. For example, an operator may hold the push button in a fully depressed position for a certain period of time, and then continuously squeezes the inflation bulb at a frequency as desired.

In the above embodiments, the operation cycle may function to clean and protect a medical instrument such as an endoscope sheath, an endoscope, an image sensor, lens or device of an endoscope, an area or location of interest, a surgical site, or a combination thereof. The operation cycle may be sufficiently long so that an image sensor, lens or device of a medical or surgical instrument is cleaned and good images can be obtained therewith. The operation cycle may be a cycle where a one or a combination of different applications, cycles, sequences, and/or functions are applied or performed. The operation cycle may be a cycle where irrigation fluid and suction are applied simultaneously, in sequence, intermittingly, on-demand, or in a combination thereof, to clean a medical or surgical instrument. The operation cycle may include an application of irrigation fluid followed immediately by an application of suction. The application cycle may apply a concurrent application of irrigation fluid and suction. The operation cycle may include only an application of irrigation fluid (i.e., a flushing cycle, a washing manner, etc.) with no suction. The operation cycle may include only an application of suction with no application of irrigation fluid. The operation cycle may be varied, adjusted, monitored, and/or controlled by a user, by one or more control modules, user interfaces, or a combination thereof.

The principles of the present disclosure may be better understood with reference to the drawings and the accompanying descriptions, wherein like reference numerals have been used throughout to designate identical or similar elements. It should be understood that these drawings are not necessarily are drawn to scale. They are presented just for illustrative purposes only, and are not intended to limit the scope of the disclosure. Examples of materials, dimensions, and constructions are included for some elements. Those of ordinary skill in the art should understand that many of the examples provided have suitable alternatives and these alternatives should also be considered within the scope of this disclosure. Moreover, certain terminology is used herein for convenience only and is not to be taken as a limitation on the present disclosure.

Figure 1:
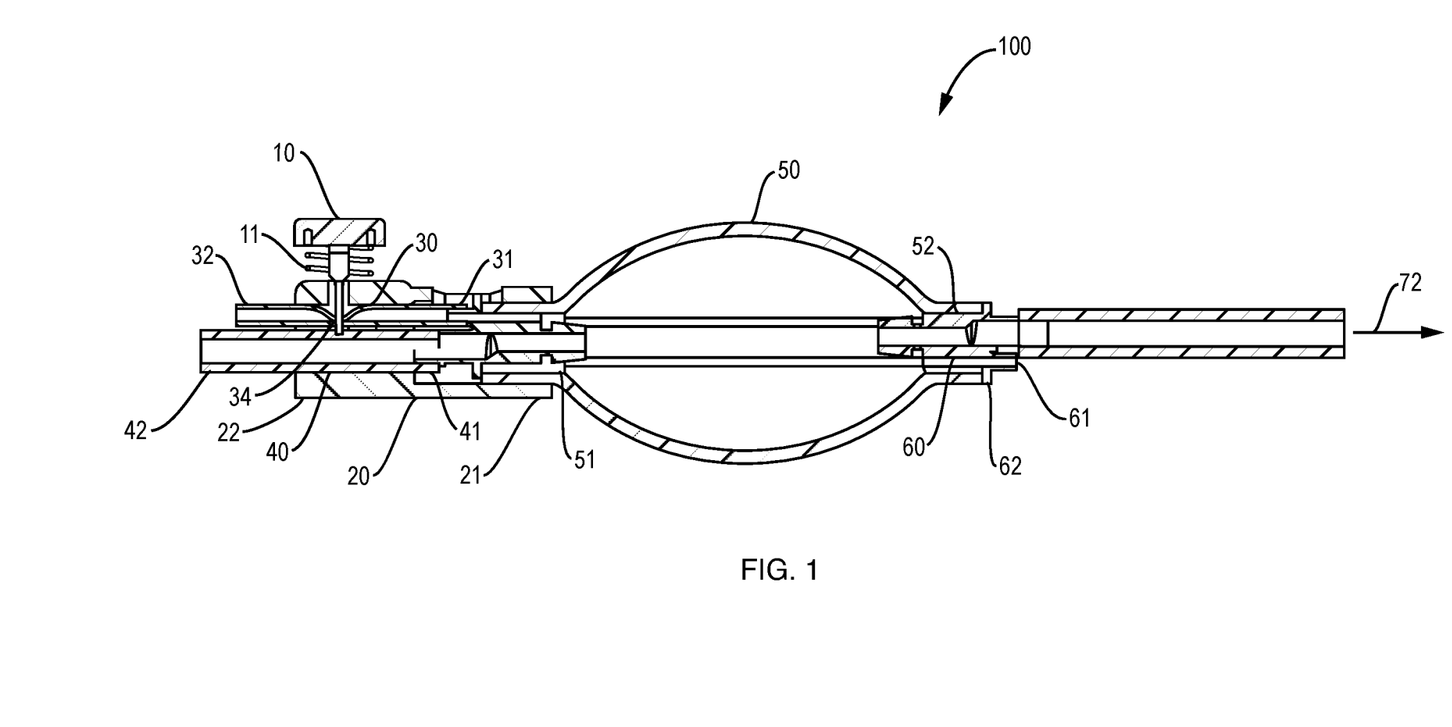
FIG. 1 is a partial longitudinal section view of a medical device in accordance with one embodiment.

FIG. 1 is a sectional view of a medical device in accordance with one aspect of the present disclosure. The medical device 100 of FIG. 1 includes a push button 10 at its resting position, a biasing member 11 such as a coil spring, a housing member 20, a first hollow member 30, a second hollow member 40, and an inflation bulb 50.

The push button 10 and the biasing spring 11 are operably connected to the housing member 20. The housing member 20 includes a proximal portion 21 and a distal portion 22. Alternatively, the housing member 20 includes a first portion and a second portion. Regardless, such designations are just to indicate that the housing member is configured to have two portions: one portion for connecting with the push button 10, the other for connecting with the inflation bulb 50. The housing member 20 is also configured to partially receive the first hollow member 30 and the second hollow member 40.

The first hollow member 30 includes a proximal end 31 and a distal end 32. It is properly disposed in the housing member 20 to ensure proper or tight sealing or clamping by the push button 10 when the push button is at its resting position. It may be received in the housing member, for example, in a groove like configuration with a suitable dimension such that it is flexibly movable along the longitudinal direction, but has limited mobility along the vertical direction. The proximal end 31 is configured to be in fluid communication with the bulb 50 while the distal end 32 is configured to be attachable to a medical or surgical instrument (not shown). As indicated in FIG. 1, the push button 10 at its resting position is configured to fully or functionally seal the first hollow member 30 from air or gas flow at position 34 of the first hollow member 30. At its resting position, the push button 10 also allows the second hollow member 40 to be at its full open position, and ready for suction to remove any irrigation liquid or cut biological material from the surgical site or the surgical instrument without any interference from the first hollow member 30.

The second hollow member 40 includes a proximal end 41 and a distal end 42. It is properly disposed in the housing member 20 to ensure proper or tight sealing or clamping by the push button 10 when the push button is depressed to its fullest extent. It may be received in the housing member, for example, in a groove like configuration with a suitable dimension such that it is flexibly movable along the longitudinal direction, but has limited mobility along the vertical direction. The proximal end 41 is configured to be connectable to the inflation bulb 50 while the distal end 42 is configured to be attachable to a medical or surgical instrument (not shown).

The inflation bulb 50 includes an opening 51 on the one end and another opening 52 on the other. The opening 51 is configured to be connectable with the distal portion 21 of the housing member 20 while the opening 52 is configured to be sealable with a connector 60. The opening 51 may be secured and sealed to the proximal end 21 of the housing member 20 through conventional means such as through glue or snap fit or welding, or any other suitable mechanisms known in the art. The opening 52 may be secured and sealed to the connector 60 through conventional means such as through glue or snap fit or welding, or any other suitable mechanisms known in the art.

The connector 60 may be configured to have a one way check valve 61. The one way check valve 61 only allows air or an inert gas to flow into the bulb 50, but not the other way around. The inert gas may be carbon dioxide, nitrogen or other suitable gases for surgical procedures. The connector 60 may be configured to have a one way air or inert gas inlet 62. The one way air or inert gas inlet 62 only allows the air or inert gas to flow into the bulb 50, but not the other way around. The connector 60 may be preferably configured to have both a one way check valve and a one way gas inlet.

As illustrated in FIG. 1, the second hollow member 40 may be configured to go straight through the interior of the inflation bulb 50 from the opening 51 to the opening 52 to a vacuum or suction source in the direction as shown by the arrow 72. It may also be configured to attach to a connector (not shown) at the opening 51 to facilitate a tight connection to the opening 51. Similarly, the connector 60 is also configured to facilitate a tight connection of the second hollow member to the opening 52. In general, the second hollow member 40 may be contemplated as a vacuum or suction line. It is configured to be properly secured and sealed with the openings 51 and 52 and/or with the connector 60 by suitable means known in the art.

Figure 2:
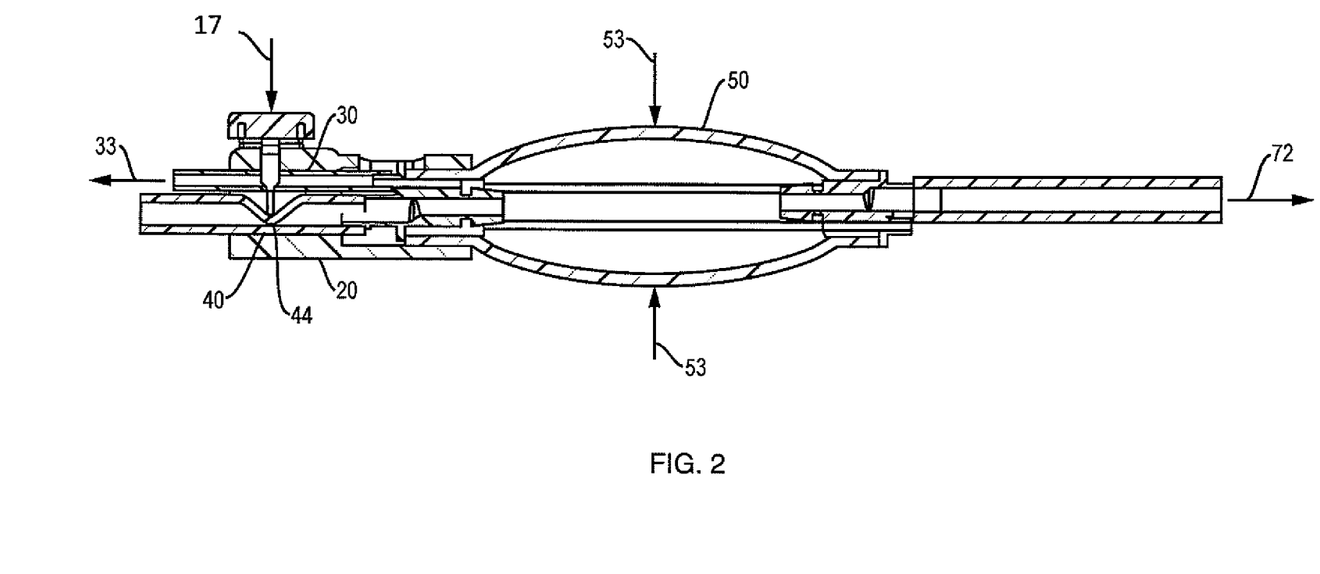
FIG. 2 is a partial longitudinal section view of a medical device in accordance with one embodiment.

"Referring to FIG. 2 for a situation when the push button 10 of the medical device 100 is depressed to its fullest extent as shown by arrow 17. Once that happens, the push button releases the first hollow member 30 from a clamped position into an open position, and squeezes the second hollow member 40 into a complete sealing at position 44. The air or inert gas will then be allowed to flow through the first hollow member 30 in the direction as shown by the arrow 33 if an operator squeezes the inflation bulb 50 in the direction as shown by arrows 53 once the second hollow member 40 is completely sealed. Depressing the push button may be accomplished by one hand, and squeezing the inflation bulb by the same hand of an operator. The depressing and the squeezing may be performed multiple times or as many times as needed. In other words, the medical device may be configured such that both the push button 10 and the inflation bulb 50 can be manipulated by just one hand of an ordinary operator for easy and convenient operation."

Figure 3:
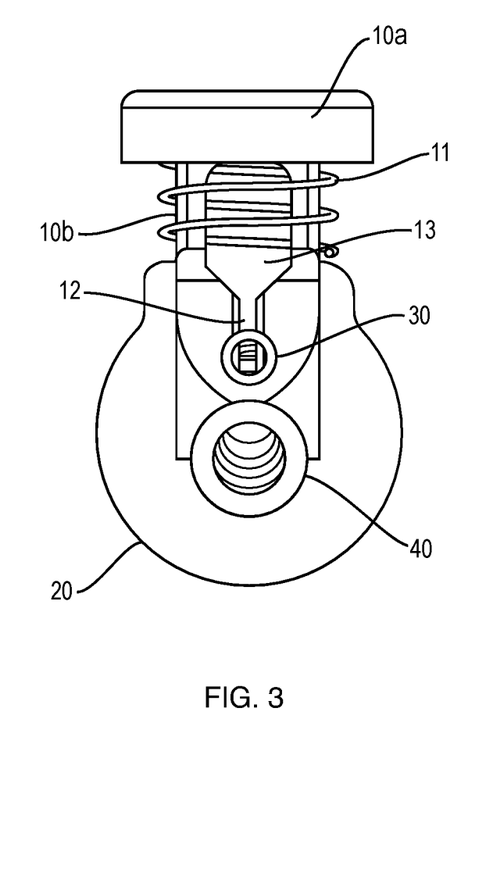
FIG. 3 is a sectional view of the push button in its resting position as shown in FIG. 1.
Figure 4:
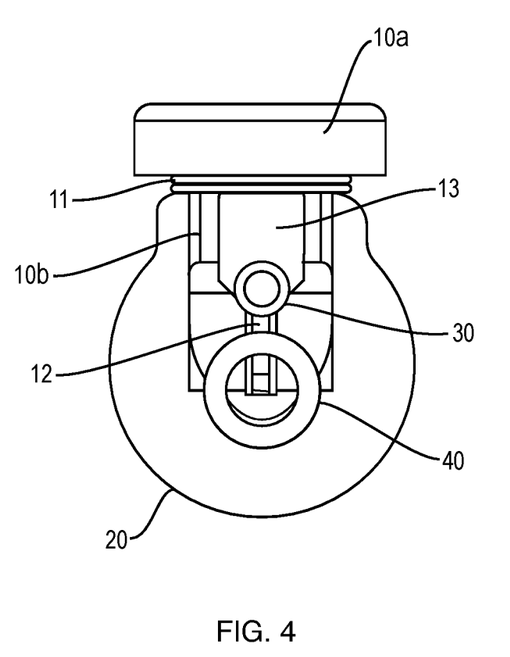
FIG. 4 is a sectional view of the push button in its fully depressed position as shown in FIG. 2.

"Referring to FIG. 3 and FIG. 4 for a more detailed description of how the push button 10 and the biasing spring 11 operate together to clamp and release the hollow members in a coordinated manner. The push button 10 has a head portion 10a and a stem portion 10b. The biasing spring 11 is fixedly secured under the head portion 10a and wrapped around the stem portion 10b through the suitable known means in the art. The body portion 10b has a narrow slot 12 at its lower end and a wider slot 13 towards its head. The narrow slot 12 is configured to completely seal off the hollow member 30 from gas flow when the push button 10 is at its resting position. The wider slot 13 is configured to allow the first hollow member a complete open position when the first hollow member 30 is pushed into the wider slot 13. The push button 10 is configured to completely seal off the second hollow member 40 when it is pushed to its full extent as shown in FIG. 4. Once the pushing force is removed or absent from the push button, the biasing spring 11 will then restore the push button back to its resting position as shown in FIG. 3."

Figure 5:
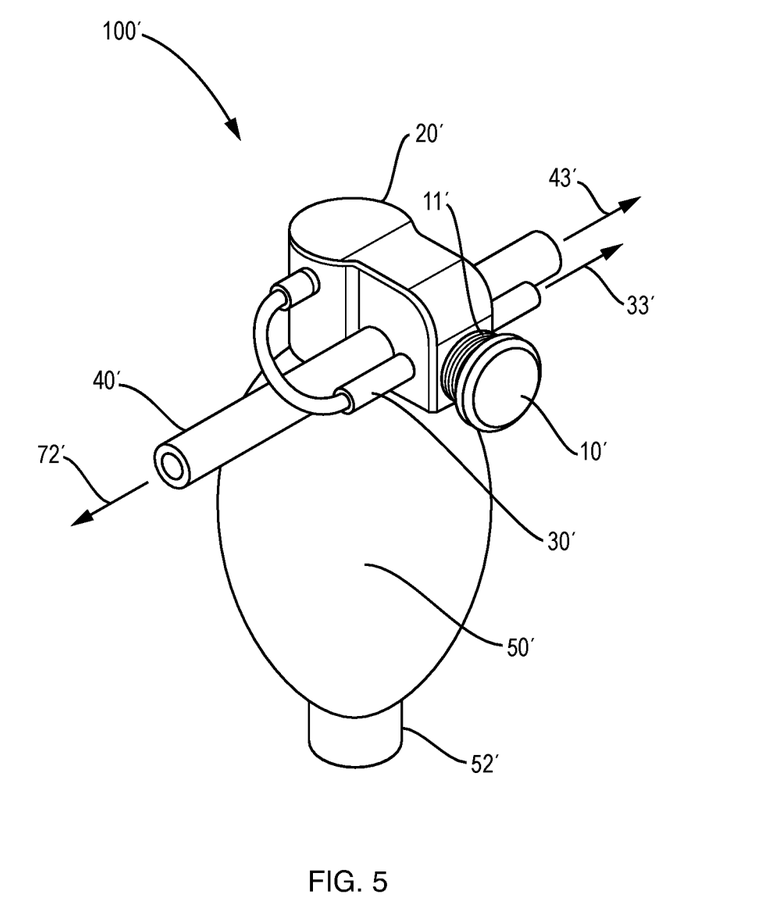
FIG. 5 is a perspective view of a medical device in accordance with another embodiment.

FIG. 5 illustrates a medical device 100' in accordance with another aspect of the disclosure. The medical device 100' of FIG. 5 includes a push button 10', a biasing spring 11', a housing member 20', a first hollow member 30', and a second hollow member 40', and an inflation bulb 50'.

As similarly described with respect to FIG. 1 and FIG. 2, the first hollow member 30' is configured to be connectable to a medical or surgical device on one end as shown by the arrow 33', and in fluid communication with the bulb 50' on the other. The second hollow member 40' is configured to be connectable to a suction source on the one end as shown by the arrow 72', and to a medical or surgical instrument on the other as shown by arrow 43'. FIG. 5 illustrates that the second hollow member 40' does not go through the interior of the inflation bulb 50'. Rather, it is completely outside of the inflation bulb 50'. The inflation bulb 50' includes two openings: 52' and 51' (not shown, but contemplated to be in fluid communication with the first hollow member 30'). The opening 52' is configured to have a one way gas inlet or a one way valve (not shown). Preferably, the inflation bulb 50' is configured to have a one way gas inlet and a one way valve. The opening 52' may be properly sealed or gas tight through suitable means known in the art.

Also as similarly described with respect to FIG. 3 and FIG. 4, the push button 10' has a narrow slot at it lower end and a wider slot at its upper end (not shown). The narrow slot is configured to completely seal off the first hollow member 30' from gas flow at its resting position while the wider slot is configured to allow the first hollow member to be completely open and completely or functionally seal off the second hollow member 40' at the same time when the push button is depressed to its fullest extent. Once the pushing force is removed or absent from the push button 10', the biasing spring 11' will then restore the push button back to its resting position, and the first hollow member is consequently fully or functionally clamped/sealed.

For a medical device as shown in FIG. 1 and FIG. 5, the push button, the housing member, the first hollow member, the second hollow member, and the inflation bulb may all be made by plastic materials or polymeric materials, or made disposable or reusable. Preferably, all the above components may be made disposable.

Figure 6:
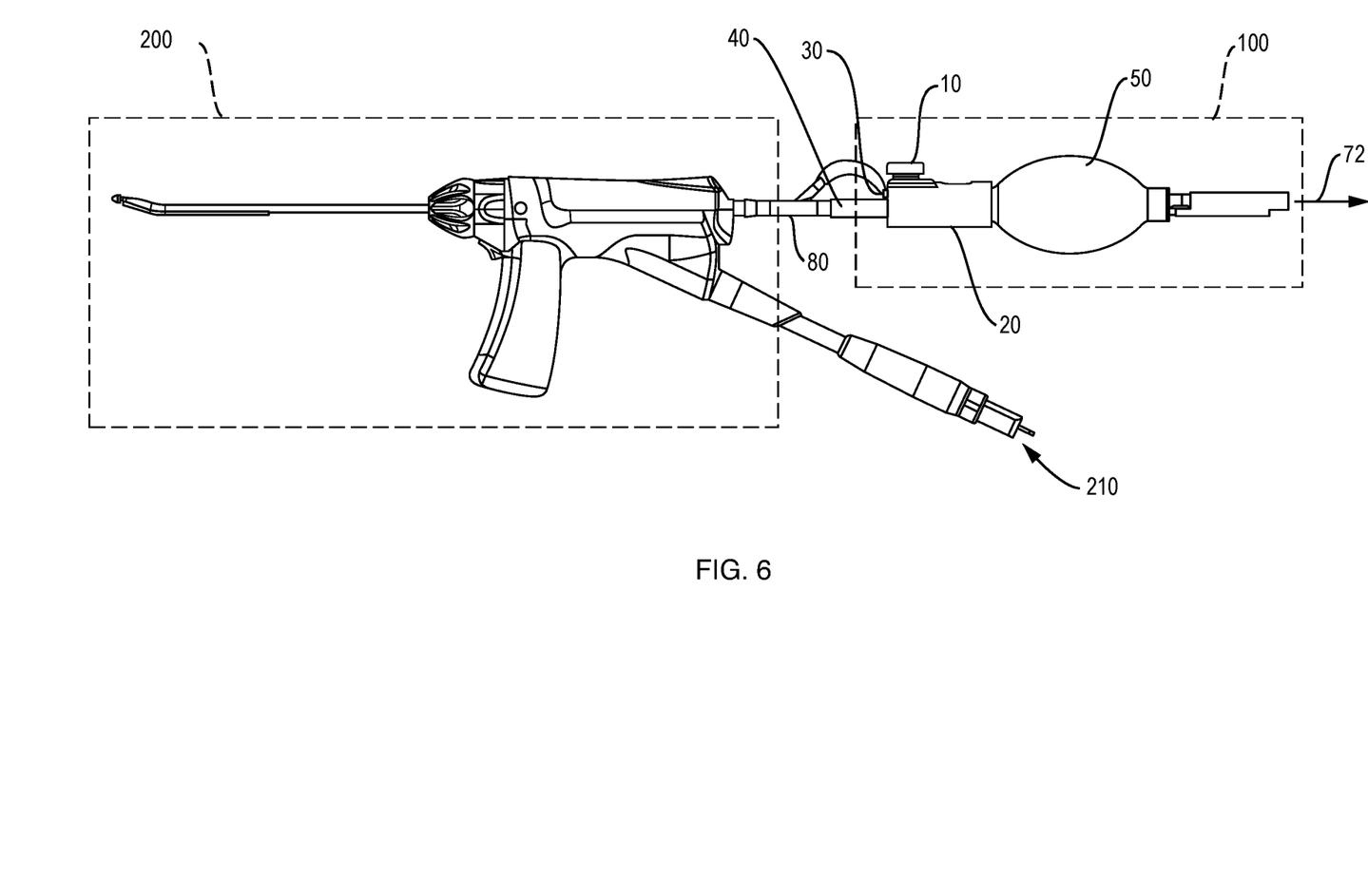
FIG. 6 is a perspective view of the medical device shown in FIG. 1 connected to a surgical instrument.

FIG. 6 is a perspective view showing a medical device 100 attached to a surgical or medical instrument 200 through a Y connector 80. The medical device 100 includes a push button 10, a housing member 20, a first hollow member 30, a second hollow member 40, and an inflation bulb 50. The first hollow member 30 is configured to connect to the surgical or medical instrument 200 through one arm of the Y connector 80, and the second hollow member 40 is configured to be connectable to the medical or surgical instrument 200 through the other arm of the connector 80. The medical or surgical instrument 200 includes an irrigation line 210. The medical or surgical instrument 200 may be a microdebrider.

During a surgical operation, the medical device 100 is attached to a medical or surgical instrument 200 through the Y connector 80 and to a vacuum or suction source as shown by the arrow 72. The medical or surgical instrument is connected to an irrigation source (not shown) through the irrigation line 210. Following proper connections of all these lines, an operator can then turn on the medical or surgical instrument 200, connect to a vacuum or suction source as shown by the arrow 72, and then squeeze the inflation bulb 50 and depress the push-button 10 to clean or de-clog an obstruction for as many times as necessary during the operation. The operator can operate the whole system simply and efficiently as desired.

These illustrative examples disclose that a medical device may be able to provide de-clogging capabilities to a surgical cutting instrument. The medical device may also be used to provide pressure and suction to other surgical devices that may require both pressure and suction; such as lavage apparatuses, ventilator lumens, endoscope cleaners, and such. Examples of some surgical devices may be found in U.S. Pat. Nos. 5,439,022 and 7,270,647; and U.S. Patent Application Publication Nos. 2006/0264995 and 2013/0289595 all of which are incorporated by reference herein for all purposes.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A medical device comprising:
   a first hollow member configured to allow air or an inert gas passage;
   a second hollow member having a distal end and a proximal end, the proximal end configured to be connectable to a vacuum or suction source;
   a housing member configured to receive both the first hollow member and the second hollow member; and
   a push button configured to be operably connected to the housing member, the push button including a head portion and a stem portion, the stem portion having a terminal end surface opposite the head portion and a slot longitudinally defined in the stem portion,
   wherein when the push button is not depressed, surfaces defining the slot are configured to engage the first hollow member and cause the first hollow member to be occluded, and
   wherein, when the push button is depressed, surfaces defining the slot are configured to disengage from the first hollow member such that the first hollow member is not occluded, and the terminal end surface of the stem portion is configured to occlude the second hollow member.

2. The medical device of claim 1, wherein the terminal end surface of the stem portion is configured to disengage the second hollow member when a force depressing the push button is removed.

3. The medical device of claim 1, wherein the medical device further comprises an inflation bulb configured to be attachable to the housing member.

4. The medical device of claim 1, wherein the distal end of the second hollow member is configured to be connectable to a medical or surgical instrument.

5. The medical device of claim 4, wherein the medical or surgical instrument comprises an irrigation line.

6. The medical device of claim 4, wherein the medical or surgical instrument is a microdebrider.

7. The medical device of claim 1, wherein the slot includes a narrow portion and a wide portion,
   the narrow portion is configured to disengage the first hollow member and the first hollow member is configured to be received into the wide portion when the push button is depressed by a force.

8. A medical device comprising:
   a first hollow member configured to allow air or an inert gas passage;
   a second hollow member having a distal end and a proximal end, the proximal end configured to be connectable to a vacuum or suction source;
   a housing member having a first section and a second section, the housing member configured to receive both the first hollow member and the second hollow member;
   a push button disposed at the first section of the housing member, the push button including a head portion and a stem portion, the stem portion having a terminal end surface opposite the head portion and a slot longitudinally defined in the stem portion; and
   an inflation bulb having two openings, one opening configured to be attached to the second section of the housing member,
   wherein the inflation bulb and the push button are configured to be operable by one hand of an operator,
   wherein when the push button is not depressed, surfaces defining the slot are configured to engage the first hollow member and cause the first hollow member to be occluded, and
   wherein, when the push button is depressed by a force, surfaces defining the slot are configured to disengage from the first hollow member such that the first hollow member is not occluded, and the terminal end surface of the stem portion is configured to occlude the second hollow member.

9. The medical device of claim 8, wherein the terminal end surface of the stem portion is configured to disengage the second hollow member when the force is removed.

10. The medical device of claim 8, wherein the medical device further comprises a connecting member.

11. The medical device of claim 10, wherein the connecting member is configured to have a one way valve.

12. The medical device of claim 10, wherein the connecting member is configured to have a one way gas inlet.

13. The medical device of claim 8, wherein the second hollow member is configured to be connectable to the vacuum or suction source through the inflation bulb.

14. The medical device of claim 8, wherein the second hollow member is configured to be connectable to the vacuum or suction source without going through the inflation bulb.

15. The medical device of claim 8, wherein the distal end of the second hollow member is configured to be connectable to a medical or surgical instrument.

16. The medical device of claim 15, wherein the medical or surgical instrument is a microdebrider.

17. The medical device of claim 15, wherein the medical or surgical instrument comprises an irrigation line.

18. The medical device of claim 8, wherein the slot includes a first slot narrow portion and a second slot that is wider than the first slot wide portion, the first slot narrow portion is configured to disengage the first hollow member and the first hollow member is configured to be pushed received into the second slot wide portion when the push button is depressed by the force.

19. A surgical system comprising:
   the medical device in accordance with claim 8;
   a surgical instrument for cutting, resecting, shaving, and/or removing tissue;
   the vacuum or suction source; and
   an irrigation source,
   wherein the medical device is operably connected to the vacuum or suction source and the surgical instrument, and wherein the irrigation source is operably connected to the surgical instrument.

20. The surgical system of claim 19, wherein the surgical instrument is a microdebrider.

\* \* \* \* \*

UNITED STATES PATENT AND TRADEMARK OFFICE
CERTIFICATE OF CORRECTION

| | | |
|---|---|---|
| PATENT NO. | : 10,702,636 B2 | Page 1 of 1 |
| APPLICATION NO. | : 15/691810 | |
| DATED | : July 7, 2020 | |
| INVENTOR(S) | : Ming J. Cheng and Phillip R. Scruggs | |

It is certified that error appears in the above-identified patent and that said Letters Patent is hereby corrected as shown below:

In the Claims

In Claim 18:
Column 17, Lines 4-5, "first slot narrow portion and a second slot that is wider than the first slot wide portion, the first slot" should be deleted and --narrow portion and a wide portion, the-- should be inserted.
Column 17, Lines 7-8, "pushed received into the second slot" should be deleted and --received into the-- should be inserted.

Signed and Sealed this
Eighteenth Day of August, 2020

Andrei Iancu
*Director of the United States Patent and Trademark Office*